United States Patent
Kolesinski (10) Patent No.: US 10,946,329 B2
(45) Date of Patent: Mar. 16, 2021

(54) SYSTEM AND METHODS FOR SEPARATING AND PURIFYING CANNABINOIDS FROM PLANT MATERIAL

(71) Applicant: PRIME SEPARATIONS, INC., Arlington, MA (US)

(72) Inventor: Henry S. Kolesinski, Naples, FL (US)

(73) Assignee: PRIME SEPARATIONS, INC., Arlington, MA (US)

( * ) Notice: Subject to any disclaimer, the term of this patent is extended or adjusted under 35 U.S.C. 154(b) by 0 days.

(21) Appl. No.: 16/688,718

(22) Filed: Nov. 19, 2019

(65) Prior Publication Data

US 2020/0155995 A1 May 21, 2020

Related U.S. Application Data (60) Provisional application No. 62/769,271, filed on Nov. 19, 2018.

(51) Int. Cl.

| | | |
|---|---|---|
| C07C 27/26 | (2006.01) | |
| B01D 53/00 | (2006.01) | |
| B01D 53/06 | (2006.01) | |
| B01D 11/02 | (2006.01) | |
| C07C 27/34 | (2006.01) | |
| B01D 11/00 | (2006.01) | |

(52) U.S. Cl.
CPC .......... *B01D 53/06* (2013.01); *B01D 11/0288* (2013.01); *C07C 27/34* (2013.01); *B01D 2011/007* (2013.01); *B01D 2257/70* (2013.01); *B01D 2259/40083* (2013.01)

(58) Field of Classification Search
CPC .......... C07C 27/26; C07C 27/34; B01D 53/06
See application file for complete search history.

(56) References Cited

PUBLICATIONS

CannabisChris, Decarboxylation of cannabis: scientific info about temps and times. Retrieved online at: cannabischris.com/2012/10/decarboxylation-of-cannabis/ 4 pages, Oct. 31, 2012.
Herb, How to Decarboxylate Your Weed. Retrieved online at: https://herb.co/guides/decarboxylate-your-weed-for-the-full psycho-active-effect/ 6 pages, Jun. 27, 2014.
Montana BioTech, Cannabinoid Facts: THC, CBD, CBN, CBC, THCV, CBG and Other Unique Phyto Cannabinoids. Retrieved online at: https://montanabiotech.com/2013/03/25/cannabinoid-facts-thc-cbd-cbn-cbc-thcv-cbg-and-other-unique-phyto-cannabinoids/ 13 pages, Mar. 25, 2013.
Wilder, What Are the Benefits and Boiling Points for Cannabis Vaporization? Retrieved online at: https://maryjane.com/health/cannabis-vaporization-benefits-boiling-points. 4 pages, Sep. 17, 2016.
Zamnesia, Vaporizer Temperatures for Cannabis—The Ultimate Guide. Retrieved online at: https://www.zamnesia.com/content/284-vaporizer-termperatures-for-cannabis. 8 pages, 2013-2020.

*Primary Examiner* — Sikarl A Whitherspoon
(74) *Attorney, Agent, or Firm* — McCarter & English, LLP; Jonathan M. Sparks (57) ABSTRACT

Methods and systems are disclosed for concentrating a compound found in plant material from one or more species of the *Cannabis* genus. A system includes a capture/heating station having at least one heating element to heat a mass of material held within the capture/heating station; at least one release station in series with and liquidly isolated from the capture/heating station, each release station defining a volume at least partially filed by a release reagent formulated to release a target product from a substrate; and a conveyor configured to carry a belt through the capture/heating station and then the at least one release station.

20 Claims, 3 Drawing Sheets

SYSTEM AND METHODS FOR SEPARATING AND PURIFYING CANNABINOIDS FROM PLANT MATERIAL

BACKGROUND OF THE TECHNOLOGY

The present application claims the benefit of priority to U.S. Provisional Patent Application No. 62/769,271, filed Nov. 19, 2018.

In the pharmaceutical industry, product purity and concentration control are of utmost importance. Unfortunately, many drug compounds are difficult, i.e., expensive, to purify and/or isolate from their source material(s). The ability to produce a specific drug compound cheaply can be the difference between the drug being widely used or too expensive for widespread use.

One particular class of compounds that have been more widely explored as pharmaceuticals in recent years are cannabinoids derived from various plant species of the *Cannabis* genus. While some cannabinoids, particularly tetrahydrocannabinol (THC), have been of interest for years due to their psychoactive effects when consumed, recent research has suggested that non-psychoactive cannabinoids, such as cannabidiol (CBD), may have beneficial medical uses that do not cause user impairment as THC does.

Large-scale, high-quality purification of CBD from plant material of various plant species of the *Cannabis* genus is not currently economical due to the relatively high price of isolating and concentrating the CBD from the plant material. Specifically, many of the purification strategies are anecdotal and not particularly sophisticated or effective. One particular type of purification strategy for CBD utilizes a short path distillation format, with purification being performed in batches and therefore generally not easily automated.

There remains a need in the art for purifying compounds from various plant species that can be performed cheaply and efficiently.

SUMMARY

The present technology relates to concentrating one or more compounds found in plant material. In particular, the present disclosure relates to systems and methods for the concentration of cannabinoids, such as CBD. The systems of the present disclosure can be used, for example, to produce high-concentration CBD products for use in treating various medical conditions.

In one exemplary embodiment provided in accordance with the present invention, a system for concentrating a compound found in plant material from one or more species of the *Cannabis* genus includes: a capture/heating station having at least one heating element configured to heat a mass of material held within the capture/heating station; at least one release station in series with and liquidly isolated from the capture/heating station, the at least one release station defining a volume at least partially filed by a release reagent formulated to release a target product from a substrate; and a conveyor configured to carry a belt through/above the capture/heating station and then the at least one release station.

In some exemplary embodiments, a belt is carried by the conveyor. The belt includes at least one functionalized surface targeted toward the target product, the release reagent being formulated to release the target product from the at least one functionalized surface. In some exemplary embodiments, the target product is a cannabinoid and/or cannabidiol.

In some exemplary embodiments, the system includes a mechanical processor in series with or held within the capture/heating station that is configured to smash, pulverize, grind, chop, and/or break plant material.

In some exemplary embodiments, the system includes a first release station defining a first volume at least partially filled by a first release reagent formulated to release the target product from the at least one functionalized surface and a second release station defining a second volume at least partially filled by a second release reagent formulated to release the target product from the at least one functionalized surface, the second release reagent being different from the first release reagent and the second release station being liquidly isolated from the first release station. In one exemplary embodiment, the conveyor is configured to carry the belt through the capture/heating station, then the first release station, then the second release station.

In some exemplary embodiments, the system includes a calibration station in series with and liquidly isolated from the capture/heating station and the at least one release station, the conveyor being configured to carry the belt through the capture/heating station, the at least one release station, and the calibration station. The calibration station defines a calibration volume at least partially filled by a calibration reagent formulated to re-calibrate at least one surface of the belt carried by the conveyor through the calibration station. In one exemplary embodiment, the conveyor is configured to carry the belt through the capture/heating station, then the at least one release station, then the calibration station.

In some exemplary embodiments, the at least one heating element is configured to reach a heating temperature between 100° C. and 230° C.; in other exemplary embodiments, the at least one heating element is configured to reach a heating temperature of at least 230° C.

In another exemplary embodiment, a method for concentrating a compound found in one or more species of the *Cannabis* genus is provided. The method includes: heating plant material to a volatilization temperature of a target product in the plant material to volatilize the target product; adsorbing the volatilized target product to a functionalized belt; and contacting at least a portion of the functionalized belt with a release reagent to release the adsorbed target product from the belt into the release reagent. In some exemplary embodiments, the contacting can include immersing at least a portion of the functionalized belt in the release reagent and/or applying the release reagent to the functionalized belt.

In some exemplary embodiments, the target product is a cannabinoid and/or cannabidiol.

In some exemplary embodiments, the method also includes mechanically processing the plant material to increase a surface area of the plant material prior to or during heating. In one exemplary embodiment, the mechanical processing includes smashing, pulverizing, grinding, chopping, and/or breaking. In some exemplary embodiments, the mechanical processing produces processed plant material having an average particle size of less than 1 mm; in certain exemplary embodiments, the average particle size is less than 100 microns, such as 10-50 microns.

In some exemplary embodiments, the volatilization temperature is between 100° C. and 230° C., with exemplary volatilization temperature ranges including but not being limited to: between 100° C. and 120° C.; between 150° C.

and 160° C.; between 170° C. and 180° C.; between 160° C. and 180° C.; between 180° C. and 190° C.; and between 180° C. and 220° C.

In some exemplary embodiments, the plant material is from at least one plant species of the *Cannabis* genus.

In some exemplary embodiments, the heating does not produce combustion of the plant material.

In some exemplary embodiments, the plant material is heated for between 1 and 120 minutes prior to the target product volatilizing; in certain exemplary embodiments, the plant material is heated for between 5 and 10 minutes prior to the target product volatilizing; in other exemplary embodiments, the plant material is heated for at least 20 minutes prior to the target product volatilizing.

In some exemplary embodiments, the plant material is heated at a first heating temperature for a first heating time period and a second heating temperature greater than the first heating temperature for a second heating time period. In some exemplary embodiments, the second heating temperature is at least 20° C. greater than the first heating temperature, such as at least 50° C. greater than the first heating temperature or at least 100° C. greater than the first heating temperature. In certain exemplary embodiments, the first heating time period is greater than the second heating time period. In some exemplary embodiments, the first heating time period is at least 5 minutes greater than the second heating time period, such as at least 10 minutes greater than the second heating time period or at least 30 minutes greater than the second heating time period.

In some exemplary embodiments, the method also includes contacting at least a portion of the functionalized belt with a second release reagent to release remaining adsorbed target product from the belt into the second release reagent. In some exemplary embodiments, at least a portion of the functionalized belt contacts more than two release agents, as required, to release substantially all of the remaining adsorbed target product from the belt into the release agents, which may comprise three contacts, four contacts, etc.

In some exemplary embodiments, the heating and adsorbing occur in a capture/heating station and the contacting occurs in at least one release station liquidly isolated from the capture/heating station. In one exemplary embodiment, the method also includes carrying the belt through the capture/heating station and the at least one release station with an endless conveyor.

Additional combinations and/or permutations of the above exemplary embodiments are envisioned as being within the scope of the present disclosure. It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

The foregoing and other features and advantages provided by the present disclosure will be more fully understood from the following description of exemplary embodiments when read together with the accompanying drawings, in which.

DETAILED DESCRIPTION

Following below are more detailed descriptions of various concepts related to, and exemplary embodiments of, methods and systems for concentrating compounds. It should be appreciated that various concepts introduced above and discussed in greater detail below may be implemented in any of numerous ways, as the disclosed concepts are not limited to any particular manner of implementation. Examples of specific implementations and applications are provided primarily for illustrative purposes.

It should be understood that, in the context of the present invention, "plant material" may refer to any material originating from a member of a species in the kingdom Plantae including, but not limited to, stalks, stems, roots, flowers, pollen, and leaves. In certain exemplary embodiments, the plant material may be from one or more plant species of the *Cannabis* genus, which may include, but is not limited to, plant species commonly referred to as *Cannabis sativa, Cannabis indica,* and *Cannabis ruderalis.* In some exemplary embodiments, the plant material may be entire plants of the *Cannabis sativa* species.

In the context of the present invention, a "target product" is any compound that may be isolated, concentrated, and/or purified from a source material. In some exemplary embodiments, the target product may be a cannabinoid, such as cannabidiol (CBD). As used herein, a "cannabinoid" refers to any compound from a group of related compounds derived from various species of plants in the *Cannabis* genus and may include, but is not limited to, CBD, tetrahydrocannabinol (THC), cannabinol, cannabigerol, cannabichromene, etc. Cannabidiol may refer to any isomer of cannabidiol or any pharmaceutically significant derivative thereof.

As used herein, reference to atoms, ions, and/or molecules "adsorbing," and variants thereof, shall be understood according to the common chemistry definition, i.e., as the adhering of atoms, ions, or molecules from a gas, liquid, or dissolved solid to a surface. Similarly, reference to "adsorption" shall be understood to be the adhesion of atoms, ions, or molecules from a gas, liquid, or dissolved solid to a surface.

Certain exemplary embodiments may provide a polymeric material or belt that includes one or more functionalized surfaces that are chemically interactive with a target product. The functionalized surface includes a moiety that exhibits a high affinity and specificity for the target product. The functionalized surface is "targeted", i.e., it specifically and efficiently interacts with and binds to the target product. The binding between the target product and the functionalized surface may be covalent or non-covalent (e.g., hydrophobic interactions, electrostatic interactions, dipole interactions, van der Waals interactions, hydrogen bonding, etc.). Most often the binding is non-covalent.

Exemplary embodiments are described below with reference to the drawings. One of ordinary skill in the art will recognize that exemplary embodiments are not limited to the illustrative embodiments, and, that components of exemplary systems, devices and methods are not limited to the illustrative embodiments described below.

Figure 1:
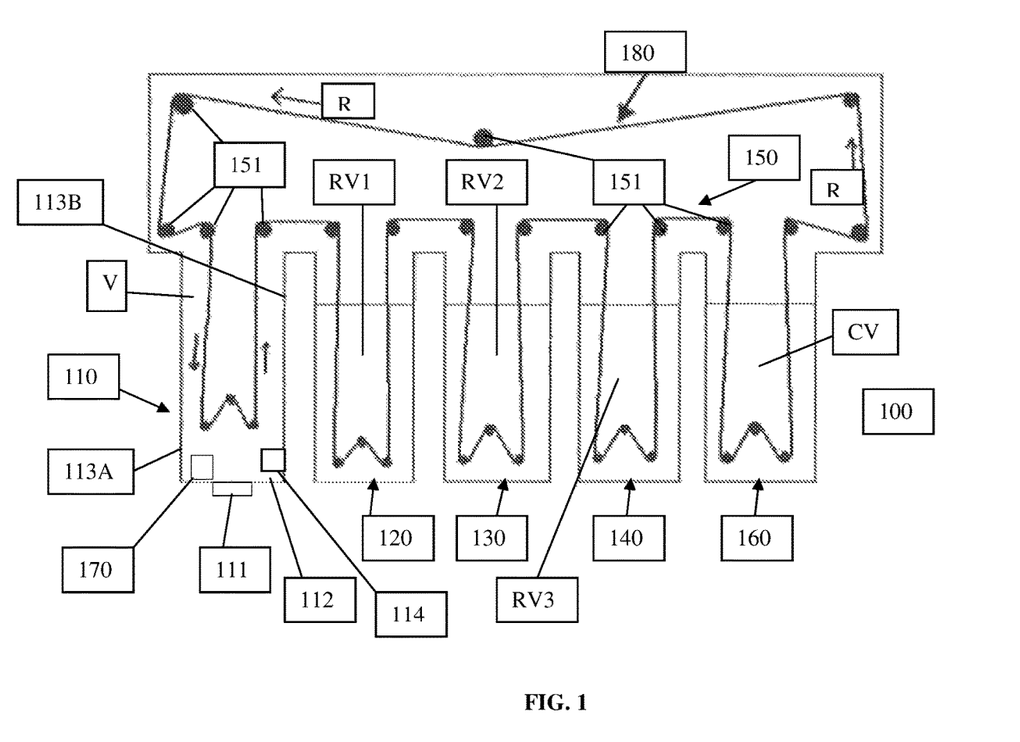
FIG. 1 is a side schematic view of an exemplary embodiment of a system formed in accordance with the present invention.

Referring specifically now to FIG. 1, an exemplary embodiment of a system 100 that can be used for concentrating compounds in accordance with the present invention is illustrated. The system 100 includes a capture/heating station 110, one or more release stations 120, 130, 140 in series with and liquidly isolated from the capture/heating station 110, and a conveyor 150 configured to carry a belt 180 through the capture/heating station 110 and then the release station(s) 120, 130, 140. In some exemplary embodiments, the system 100 also includes a calibration station 160 in series with and liquidly isolated from the capture/heating station 110 and release station(s) 120, 130, 140, as will be described further herein. Also illustrated in FIG. 1 is a belt 180 carried by the conveyor 150, which may have at least one functionalized surface, as will be described further herein.

The capture/heating station 110, as shown, defines a capture/heating station volume V and includes one or more heating elements 111 configured to heat a mass of material held within the capture/heating station 110, as will be described further herein. The capture/heating station 110 may include, for example, an open or closed chamber defining the capture/heating station volume V. In some exemplary embodiments, the heating element(s) 111 are resistive heater elements associated with a bottom surface 112 of the capture/heating station 110 that provide a heated surface to heat material resting at the bottom of the capture/heating station 110; in other exemplary embodiments, additional heating elements 111 may also be provided on side surfaces 113A, 113B of the capture/heating station 110 to heat material held in the capture/heating station 110. In still other embodiments, the heating element(s) 111 may be a furnace or similar element that turns combustion of fuel into heat in order to heat material in the capture/heating station 110; in other exemplary embodiments, the heating element(s) 111 may provide heated fluid, such as de-humidified or humidified air, to heat the material in the capture/heating station 110. It should therefore be appreciated that the manner by which the heating element(s) 111 heat the material in the capture/heating station 110 may be modified, as desired, in accordance with the present invention.

In some exemplary embodiments, the heating element(s) 111 may be configured to heat a material in the capture/heating station 110 to a volatilization temperature of a target product, which will be described further herein. In certain exemplary embodiments, the heating element(s) 111 may be configured to reach a heating temperature between 100° C. and 230° C.; for example, the heating element(s) 111 may be configured to reach a heating temperature between 160° C. and 180° C. or at least 230° C. It should be appreciated that the heating temperature of the heating element(s) 111 can be adjusted depending on the volatilization temperature of the target product and/or combustion temperature of the material being fed into and/or held within the capture/heating station 110, and therefore the previously described heating temperature are exemplary only.

In one exemplary embodiment, the heating element(s) 111 may be associated with one or more conveyor belts (not shown) in the capture/heating station 110 that conveys material as the material is heated by the heating element(s) 111 and, ultimately, conveys the heated material to a material receptacle at the end of the heated conveyor belt(s). The heated conveyor belt(s) may, in some exemplary embodiments, be rotated by one or more heated rollers that heat the conveyor belt(s), and thus any material that is placed on the surface(s) of the conveyor belt(s) and transported by the conveyor belt(s). In some exemplary embodiments, there may be a series of heating elements having different heating temperatures. There may be, for example, one or more first heating elements configured to reach a first heating temperature and one or more second heating elements configured to reach a second heating temperature that is greater than the first heating temperature. For example, the first heating element(s) may be configured to reach a first heating temperature of 100° C. while the second heating element(s) may be configured to reach a second heating temperature of between 160° C. and 180° C., the significance of which is described further herein.

The capture/heating station 110 may also include one or more air flow generators 114 to produce air flow in the capture/heating station 110, which will be described further herein. The air flow generator(s) 114 may be, for example, a fan, blower, vacuum, or other element that causes increased movement of air within the capture/heating station 110. In some exemplary embodiments, the air flow generator(s) 114 may have air flow ratings, measured in cubic feet per minute (CFM), of at least 100 CFM, at least 1,000 CFM, at least 5,000 CFM, etc. The generated air flow may be directed at the belt 180 to direct volatilized target products toward the belt 180, as will be described further herein. It should be appreciated that the air flow rating(s) of the air flow generator(s) 114 may be adjusted, as desired, and the foregoing examples should not be construed as limiting.

In some exemplary embodiments, the system 100 also includes a mechanical processor 170 that is in series with or held within the capture/heating station 110. The mechanical processor 170 may be any device that is configured to mechanically interact with a material, such as plant material, to increase the surface area of the material. In some exemplary embodiments, the mechanical processor 170 is configured to smash, pulverize, grind, chop, and/or break material that is to be fed to or held within the capture/heating station 110; in certain exemplary embodiments, the mechanical processor 170 is configured to smash, pulverize, grind, chop, and/or break plant material, such as plant material from members of the species *Cannabis sativa*. The mechanical processor 170 may be, for example, blades that rotate or reciprocate to chop apart plant material held in the capture/heating station 110. In some exemplary embodiments, the mechanical processor 170 may be configured to increase the surface area of the material by reducing the average particle size of the material in the capture/heating station 110. In certain exemplary embodiments, the mechanical processor 170 may be configured to produce material having an average particle size of less than 1 mm, such as less than 100 microns or 10-50 microns. The mechanical processor 170 may be configured, for example, to process raw plant material into fine dust for heating.

Figure 2:
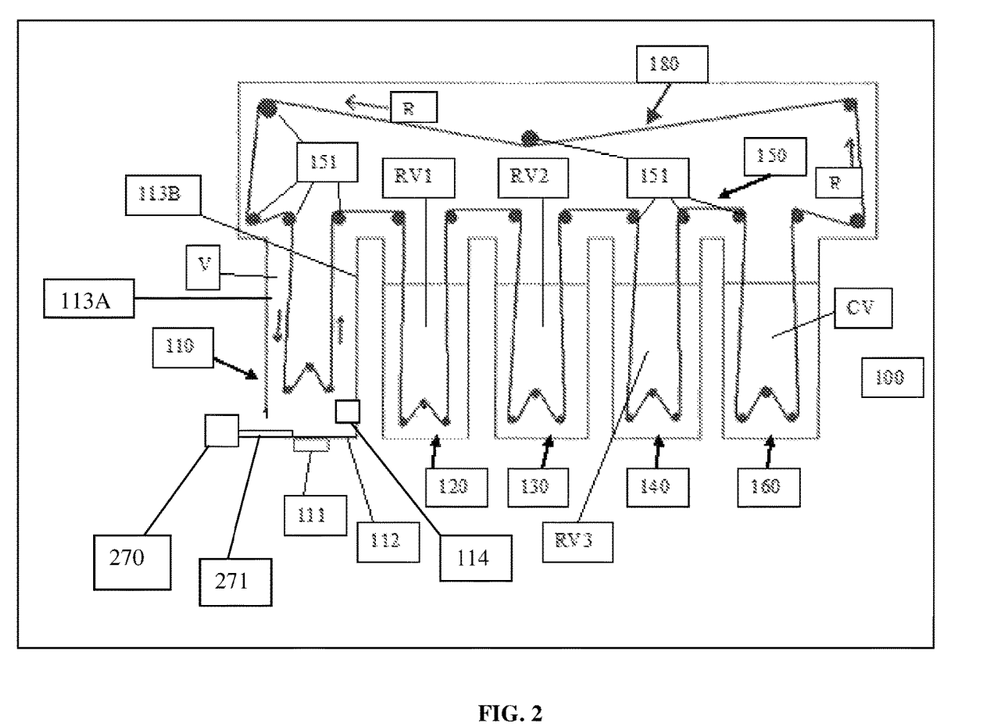
FIG. 2 is a side schematic view of another exemplary embodiment of a system formed in accordance with the present invention.

In an alternative exemplary embodiment illustrated in FIG. 2, a mechanical processor 270 may be in series with the capture/heating station 110 and include a processor conveyor 271 configured to feed processed material to the capture/heating station 110. The processor conveyor 271 may be a heated conveyor belt, as previously described, that reaches a first heating temperature to, for example, dry processed plant material prior to heating by the heating element(s) 111. In some exemplary embodiments, the mechanical processor 170 may also heat the material in the capture/heating station 110 while processing the material, i.e., the mechanical processor 170 can also act as the one or more heating elements; for example, the mechanical processor 170 may include one or more friction pads that rub and break apart plant material, while also producing sufficient heat during the rubbing to volatilize certain compounds in the plant material due to friction. Many different types of mechanical processors for processing plant material are known, so further description is omitted for brevity.

As can be seen in FIG. 1, the conveyor 150 may include a plurality of rollers 151 that can carry the belt 180 through the capture/heating station 110. In one exemplary embodiment, the rollers 151 are arranged in a loop to act as an endless conveyor for a carried belt 180, i.e., rotation of the rollers 151 causes continuous movement of the carried belt 180 through the loop, as illustrated by arrows R. In some exemplary embodiments, multiple rollers 151 may be placed in the capture/heating station 110, with the number and placement of the rollers 151 being adjustable to adjust an amount of surface area of the carried belt 180 that is in the capture/heating station 110 at any given time, which will be described further herein. In some exemplary embodiments, the rollers 151 may not form a continuous loop, and include a winding roller (not shown) that winds the carried belt 180 into a roll at the end of the conveyor 150.

The belt 180 may be any type of belt that can provide a surface for adsorption of target product molecules, as will be described further herein. One particular type of belt that may be utilized is described in U.S. Pat. No. 7,285,219 to Kolesinski et al., which is incorporated in its entirety herein by reference; the belt 180 may also be referred to as a "web," with both terms being used interchangeably herein. The belt 180 comprises a substrate, which may be of any suitable material including naturally-occurring and synthetic materials. Typical suitable materials include synthetic organic materials, metallic materials, fibrous materials such as nonwoven and woven fibers, membrane structures and any material capable of being formed into a self supported web, or sheet. Examples of useful synthetic polymeric materials are polyesters, cellulosics, polyamides, polyolefins, polyvinyl polymers, etc. Metal films such as aluminum may be employed. Films of metallized plastics are also useful. Many types of woven and non-woven fabrics would find utility as suitable belt/web materials as would other membrane structures.

The substrate of the web 180 may be of any suitable thickness and may also be subcoated with a suitable material to enhance adhesion of a capture material to the surface of the substrate. A layer of a hydrophilic polymer such as gelatin may be coated on the surface of the substrate for this purpose.

The chemical functionalization of the belt/web materials, can be by coating and immobilizing functional polymers and/or functional monomers onto the surface(s) of the supports. Coating can be accomplished by techniques known to those skilled in the art. The web substrate may be coated using a slot head coater or by dip coating, gravure roll, reverse roll or other coating methods. The chosen coating method in any particular instance will be dependent primarily on the type of support and material and application. In some instances, direct chemical reaction with the support material may be the preferred technique to chemically modify the belt/web support material with the capture material. For example, where an organic polymeric material is used as the substrate, it may be desired to employ direct chemical modification of the substrate by reaction of the substrate material with a functional monomeric or polymeric material.

To concentrate a target product, the belt 180 may include one or more functionalized surfaces that are targeted toward the target product. As used herein, a surface is "functionalized" and "targeted toward a target product" according to the present invention if the surface has characteristics that allow spontaneous adsorption of the target product to the functionalized surface; reference is made to Kolesinski et al. as teaching various strategies for functionalizing a surface in accordance with the present invention. In one exemplary embodiment, one or more ligands specifically targeted toward the target product may be bound to the functionalized surface to efficiently capture the target molecule for concentrating, as will be described further herein.

In some exemplary embodiments, the target product may be a cannabinoid, such as cannabidiol (CBD). When CBD is the target product, one or more surfaces of the belt 180 may be functionalized, as described previously, with a ligand that specifically targets CBD molecules for adhesion to the belt 180. In one exemplary embodiment, the source of CBD molecules can be plant material from one or more plants containing CBD, such as plants of the species *Cannabis sativa*, that has been placed within the capture/heating station 110 and heated to at least a volatilization temperature of CBD by the heating element(s) 111 so the CBD in the plant material is released from the solid plant material as gaseous molecules. In some exemplary embodiments, the plant material is heated by the heating element(s) 111 to or above the volatilization temperature of CBD, which is generally understood to be the boiling point of CBD, but not to the combustion temperature of the plant material. The boiling point of CBD is generally understood to be between 160° C. and 180° C., while the combustion temperature of plant material of *Cannabis sativa* is generally understood to be between 210° C. and 230° C., depending upon the moisture content of the plant material. By heating the plant material to or above the volatilization temperature of CBD but below the combustion temperature of the plant material, gaseous CBD can adhere to the belt 180 with fewer undesired gaseous molecules produced in the capture/heating station 110 that may foul the belt 180 and/or capture/heating station 110.

Once the target product has been adsorbed to the belt 180 in the capture/heating station 110, the conveyor 150 can carry the belt 180 with the adsorbed target product to the one or more release stations 120, 130, 140 that are liquidly isolated from the capture/heating station 110. As used herein, the release stations 120, 130, 140 are "liquidly isolated" from the capture/heating station 110 in the sense that liquids held in, for example, chambers of the release stations 120, 130, 140 do not spontaneously flow into the capture/heating station 110 without the use of, for example, a pump or other liquid displacement mechanism. Each of the release stations 120, 130, 140 defines a respective release station volume RV1, RV2, RV3 that is at least partially filed by a release reagent that is formulated to release the target product from a substrate, which in the exemplary embodiment is the functionalized surface(s) of the belt 180 with the adsorbed target product, into the release reagent. In some exemplary embodiments, each individual release station 120, 130, 140 is at least partially filed by a respective release reagent that differs from the release reagents in the other release stations, i.e., each release station 120, 130, 140 is at least partially filled by a different release reagent, with the release stations 120, 130, 140 each being liquidly separate from the other release stations. As described herein, the release reagents are described as being liquid solutions, but it should be appreciated that the release reagents may also be gaseous. In some exemplary embodiments, the release reagents may differ from each other by virtue of their chemical composition or, if the release reagents comprise the same compounds, by the relative concentrations of the compounds in the release reagent. In some exemplary embodiments, the release reagent(s) is formulated to cause desorption of the target product from the functionalized surface(s) of the belt 180 and release into the reagent; in some exemplary embodiments, the release reagent(s) may comprise aqueous mixtures of organic solvents including acetonitrile, alcohols and the like, or salt solutions for releasing CBD or other cannabinoids from one or more functionalized surfaces of the belt 180. Desorption of the target product from the belt 180 may also be influenced by manipulation of temperature within the individual release station 120, 130, 140. Strategies for formulating release reagent(s) to target products are described in Kolesinski et al., so further description is omitted for brevity.

The system 100 may further include a calibration station 160 in series with and liquidly isolated from the capture/heating station 110 and the release station(s) 120, 130, 140, with the conveyor 150 being configured to carry the belt 180 through the capture/heating station 110, then the release station(s) 120, 130, 140, and then through the calibration station 160. The calibration station 160 defines a calibration volume CV that is at least partially filled by a calibration reagent formulated to re-calibrate at least a portion of the belt 180 carried through the calibration station 160 by the conveyor 150. In this sense, the calibration station 160 can prepare the portions of the belt 180 carried through the calibration reagent for another concentration cycle through the system 100. The calibration reagent may, for example, be formulated to release and remove any remaining adsorbed molecules from the belt 180, whether the molecules are target product molecules or not. In some exemplary embodiments, the calibration reagent may comprise at least one of an organic solvent, such as alcohol or acetone, and a wash solution, such as distilled water or a detergent. It should be appreciated that the previously described calibration reagents can be chosen to particularly prepare the belt 180 for another concentration cycle, and therefore the foregoing calibration reagents are merely exemplary. In some exemplary embodiments, the calibration station 160 may also include one or more scrubbers (not shown), such as a cleaning roll, that are placed in contact with the belt 180 to remove adsorbed molecules from the surface of the belt 180.

Each of the stations 110, 120, 130, 140, 160 may be modular stations that can be added to, or removed from, the system 100, depending on the target product to be concentrated. For example, in some exemplary embodiments the system 100 may only include two release stations, rather than three, or may include four or more release stations with increasingly concentrated release reagents held therein. Similarly, the stations may be replaceable as needed due to, for example, corrosion of material in the station that detrimentally affects performance. In some exemplary embodiments, each of the stations 110, 120, 130, 140, 160 may be supported by a surface, such as the ground, without connection to the surface; in other exemplary embodiments, one or more of the stations 110, 120, 130, 140, 160 may be affixed to the surface using, for example, bolts and/or other connectors to firmly adhere the stations 110, 120, 130, 140, 160 in place. When it is desired to add a new station to the system 100 and/or remove one of the current stations from the system 100, the other stations of the system 100 can be relocated, if necessary, to make room for the new station and/or account for removal of the station. It should therefore be appreciated that exemplary embodiments of systems formed in accordance with the present invention may provide modular systems that can be easily tailored to concentrate various different target products utilizing the same general principles.

Figure 3:
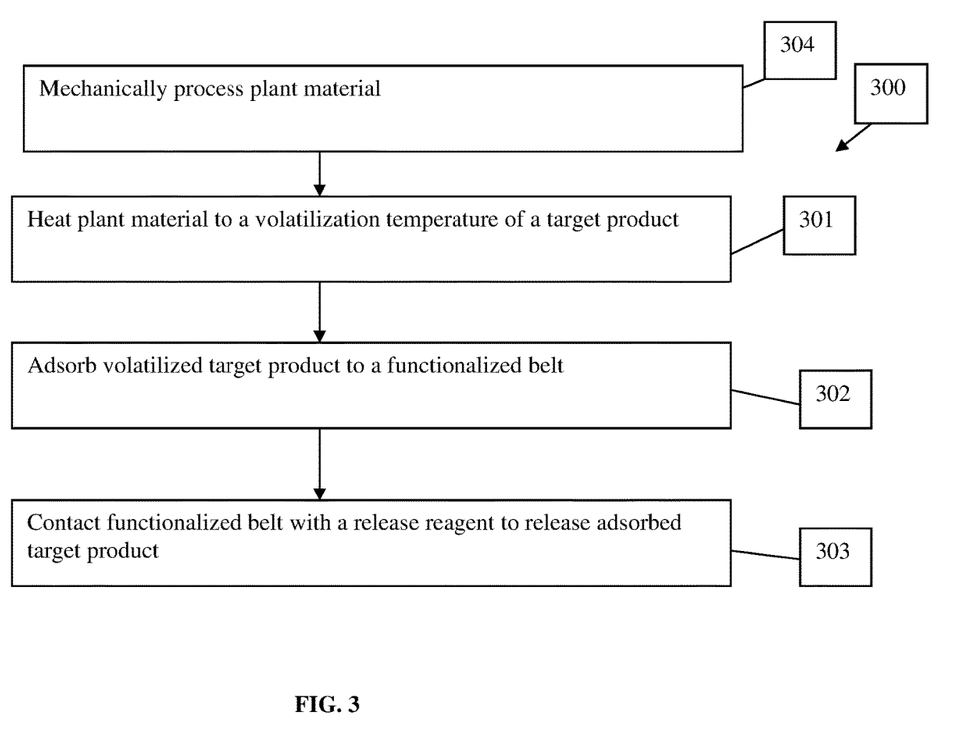
FIG. 3 is a flow chart illustrating an exemplary embodiment of a method provided in accordance with the present invention.

Referring now to FIG. 3, a flow chart illustrating an exemplary embodiment of a method 300 for concentrating a compound provided in accordance with the present invention is shown. The method 300 includes heating 301 plant material to a volatilization temperature of a target product in the plant material to volatilize the target product. The plant material may be from at least one plant species of the *Cannabis* genus, such as plants of *Cannabis sativa* commonly known and referred to as "hemp" having a relatively high concentration of CBD and a relatively low concentration of THC in the raw plant material.

In some exemplary embodiments, the target product is a cannabinoid, such as CBD, with a volatilization temperature between 100° C. and 230° C. and the heating 301 does not produce combustion of the plant material. In some exemplary embodiments, the plant material may be heated to a volatilization temperature of between 100° C. and 120° C.; between 150° C. and 160° C.; between 170° C. and 180° C.; between 160° C. and 180° C.; between 180° C. and 190° C.; and between 180° C. and 220° C. The plant material may be heated for between 1 and 120 minutes prior to the target product volatilizing. For example, the plant material may be heated: for between 1 and 5 minutes prior to the target product volatilizing; for between 5 and 10 minutes prior to the target product volatilizing; for between 10 and 20 minutes prior to the target product volatilizing; or for at least 20 minutes prior to the target product volatilizing.

The heating 301 may not only volatilize the target product, such as CBD, but also simultaneously cause conversion of an inactive precursor product into the target product. For example, many cannabinoids in the raw plant material of the *Cannabis* genus are naturally in their acid forms, which do not readily cause any change in biological function when consumed by a user. As is known, heating the plant material to certain temperatures causes spontaneous de-carboxylation of the cannabinoids to their active, non-acid forms, which do cause change in biological function when consumed by a user. Thus, the heating 301 may be performed at a heating temperature for a heating time period that both decarboxylates the cannabinoid target product(s) and volatilizes the cannabinoid target product(s). The heating 301, therefore, may not only volatilize the target product for concentration, but also convert an inactive precursor product into an active target product by de-carboxylating the raw acidic cannabinoids.

In certain exemplary embodiments, the plant material can be heated 301 to a plurality of heating temperatures for a plurality of respective heating periods. In some exemplary embodiments, the heating 301 can comprise heating the plant material at a first heating temperature for a first heating time period and a second heating temperature greater than the first heating temperature for a second heating time period. The first heating temperature may, for example, be between 80° C. and 100° C. for a time period of at least 20 minutes to remove moisture from the plant material, while the second heating temperature may, for example, be between 100° C. and 230° C. for a time period of between 5 and 10 minutes to both de-carboxylate an inactive precursor product in the dried plant material to a target product and volatilize the target product from the dried plant material. It should be appreciated that the previously described first heating temperature and respective first heating time period and second heating temperature and respective second heating time period are exemplary only, and the heating temperature(s) and respective time period(s) can be adjusted as desired.

The volatilized target product adsorbs 302 to a functionalized belt 180, which may have one or more functionalized surfaces that capture/heating the target product, as previously described. The previously described air flow generator(s) 114 can be located and oriented to direct the volatilized target product toward the functionalized belt 180 to increase the rate at which the volatilized target product adsorbs 302 to the functionalized belt 180 and minimize the amount of volatilized target product that adsorbs to surfaces not on the functionalized belt 180. At least a portion of the functionalized belt 180 is contacted 303 by a release reagent to release the adsorbed target product from the belt 180 into the release reagent, concentrating the target product in the release reagent; the contacting 303 may include, for example, immersing at least a portion of the functionalized belt 180 in the release reagent and/or applying the release reagent to at least a portion of the functionalized belt 180 by, for example, spraying. In some exemplary embodiments, the heating 301 and adsorbing 302 may occur in a capture/heating station 110 and the contacting 303 may occur in at least one release station 120, 130, 140 that is liquidly isolated from the capture/heating station 110, as previously described. In some exemplary embodiments, the contacting 303 may also comprise contacting at least a portion of the belt 180 with a second release reagent to release remaining adsorbed target product from the belt 180 into the second release reagent; in some embodiments, at least a portion of the belt 180 may be contacted by a third release reagent, fourth release reagent, etc. to remove substantially all remaining adsorbed target product on the functionalized belt 180 into the respective release reagent. A conveyor 150, such as an endless conveyor, may carry the belt 180 through and/or above the capture/heating station 110 and release station(s) 120, 130, 140.

Prior to or during the heating 301, the plant material may be mechanically processed 304 to increase a surface area of the plant material; in some exemplary embodiments, the mechanical processing 304 may comprise smashing, pulverizing, grinding, chopping, and/or breaking. The mechanical processing 304 may, for example, reduce the average particle size of the plant material, which may be from *Cannabis sativa* plants, to be less than 1 mm, such as less than 100 microns or between 10 and 50 microns. Unlike plant material of *Cannabis sativa* intended for smoking or "vaporizing," which generally has average particle sizes greater than 1 mm to prolong the time the user has to consume cannabinoids from the plant material, the mechanical processing 304 can turn the raw plant material into very fine particles, such as dust, that can rapidly heat up to the desired volatilization temperature to volatilize the target product from the raw plant material.

The previously described system 100 and method 300 can allow for efficient and cheap concentration of various target products, such as cannabinoids, from material, such as plant material. By heating 301 the material to a volatilization temperature to volatilize the target product, the raw source material, such as plant material, does not need to be soaked to release the target compound into a dilute liquid solution, which can eliminate a step and/or the use of costly reagents. The heating 301 may also convert an inactive precursor product of the plant material into the active target product, eliminating the need to treat the plant material prior to heating 301. Further, the ability of the system 100 and method 300 to operate continuously in a loop can allow for rapid concentration of target products from plant material by eliminating the "batch" aspects of the concentrating. Thus, exemplary embodiments provided in accordance with the present invention are well-suited for industrial-scale concentration of cannabinoids, such as CBD, from raw plant material, allowing large amounts of plant material to be processed into highly concentrated and pure CBD solutions.

In describing example embodiments, specific terminology is used for the sake of clarity. For purposes of description, each specific term is intended to at least include all technical and functional equivalents that operate in a similar manner to accomplish a similar purpose. Additionally, in some instances where a particular example embodiment includes system elements, device components or method steps, those elements, components or steps can be replaced with a single element, component or step. Likewise, a single element, component or step can be replaced with a number of elements, components or steps that serve the same purpose. Moreover, while example embodiments have been shown and described with references to particular embodiments thereof, those of ordinary skill in the art will understand that various substitutions and alterations in form and detail can be made therein without departing from the scope of the disclosure. Further still, other aspects, functions and advantages are also within the scope of the disclosure.

What is claimed is:

1. A system for concentrating a compound found in plant material from one or more species of the *Cannabis* genus, comprising:
   a capture/heating station having at least one heating element configured to heat a mass of material held within the capture/heating station;
   at least one release station in series with and liquidly isolated from the capture/heating station, the at least one release station defining a volume at least partially filled by a release reagent formulated to release a target product from a substrate; and
   a conveyor configured to carry a belt through the capture/heating station and then the at least one release station.

2. The system of claim 1, further comprising a belt carried by the conveyor, the belt including at least one functionalized surface targeted toward the target product, the release reagent being formulated to release the target product from the at least one functionalized surface.

3. The system of claim 2, wherein the target product is at least one of a cannabinoid and cannabidiol.

4. The system of claim 2, further comprising a mechanical processor one of in series with and held within the capture/heating station, the mechanical processor being configured to at least one of smash, pulverize, grind, chop, and break plant material.

5. The system of claim 4, wherein the mechanical processor is held within the capture/heating station.

6. The system of claim 2, wherein the at least one release station comprises a first release station defining a first volume at least partially filled by a first release reagent formulated to release the target product from the at least one functionalized surface and a second release station defining a second volume at least partially filled by a second release reagent formulated to release the target product from the at least one functionalized surface, the second release reagent differing from the first release reagent and the second release station being liquidly isolated from the first release station.

7. The system of claim 6, wherein the conveyor is configured to carry the belt through the capture/heating station, then the first release station, then the second release station.

8. The system of claim 2, further comprising a calibration station in series with and liquidly isolated from the capture/heating station and the at least one release station, the conveyor being configured to carry the belt through the capture/heating station, the at least one release station, and the calibration station, the calibration station defining a calibration volume at least partially filled by a calibration reagent formulated to re-calibrate at least one surface of the belt carried by the conveyor through the calibration station.

9. The system of claim 8, wherein the conveyor is configured to carry the belt through the capture/heating station, then the at least one release station, then the calibration station.

10. The system of claim 2, wherein the at least one heating element is configured to reach a heating temperature between 100° C. and 230° C.

11. A method for concentrating a compound found in one or more species of the *Cannabis* genus, comprising:
  heating plant material to a volatilization temperature of a target product in the plant material to volatilize the target product;
  adsorbing the volatilized target product to a functionalized belt; and
  contacting at least a portion of the functionalized belt with a release reagent to release the adsorbed target product from the functionalized belt into the release reagent.

12. The method of claim 11, wherein the target product is at least one of a cannabinoid and cannabidiol.

13. The method of claim 11, further comprising mechanically processing the plant material to increase a surface area of the plant material one of prior to and during the heating.

14. The method of claim 13, wherein the mechanical processing comprises at least one of smashing, pulverizing, grinding, chopping, and breaking.

15. The method of claim 11, wherein the volatilization temperature is between 160° C. and 180° C.

16. The method of claim 11, wherein the plant material is from at least one plant species of the *Cannabis* genus.

17. The method of claim 11, wherein the heating does not produce combustion of the plant material.

18. The method of claim 11, further comprising contacting at least a portion of the functionalized belt in a second release reagent to release remaining adsorbed target product from the belt into the second release reagent.

19. The method of claim 11, wherein the heating and adsorbing occur in a capture/heating station and the contacting occurs in at least one release station liquidly isolated from the capture/heating station.

20. The method of claim 19, further comprising carrying the belt through the capture/heating station and the at least one release station with an endless conveyor.

* * * * *